United States Patent
Olsen et al.

(10) Patent No.: US 9,539,082 B2
(45) Date of Patent: Jan. 10, 2017

(54) TISSUE SUPPORT STRUCTURE

(75) Inventors: Timothy W. Olsen, Atlanta, GA (US); David W. Rosen, Marietta, GA (US); Shreyes N. Melkote, Roswell, GA (US); George K. Mathai, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 233 days.

(21) Appl. No.: 13/511,690

(22) PCT Filed: Nov. 24, 2010

(86) PCT No.: PCT/US2010/058090
§ 371 (c)(1),
(2), (4) Date: Dec. 7, 2012

(87) PCT Pub. No.: WO2011/066451
PCT Pub. Date: Jun. 3, 2011

(65) Prior Publication Data
US 2013/0073054 A1    Mar. 21, 2013

Related U.S. Application Data

(60) Provisional application No. 61/264,081, filed on Nov. 24, 2009.

(51) Int. Cl.
*A61F 2/02* (2006.01)
*A61F 9/007* (2006.01)

(52) U.S. Cl.
CPC .............. *A61F 2/02* (2013.01); *A61F 9/00727* (2013.01); *A61F 2210/0019* (2013.01); *A61L 2400/16* (2013.01); *C08L 2201/12* (2013.01)

(58) Field of Classification Search
CPC  A61F 2/02; A61F 9/00727; A61F 2210/0019; A61F 2/147; A61L 2400/16; C08L 2201/12; A61B 17/122; A61B 17/128; A61B 17/064; A61B 17/0644; A61B 17/1227; A61B 17/0057; A61B 2017/0645; A61B 2017/0649; A61B 17/00575; A61B 17/00584; A61B 17/00588; A61B 17/00592; A61B 17/00623; A61B 17/00619; A61B 17/00606; A44B 19/406; A44B 19/40; A44B 19/403; A44B 19/50; Y10T 24/44923; Y10T 24/44889; Y10T 24/44769; Y10T 24/44
(Continued)

(56) References Cited

U.S. PATENT DOCUMENTS 3,927,471 A    12/1975   Tricker
4,043,564 A    8/1977    White
(Continued)

FOREIGN PATENT DOCUMENTS

EP    1447064 A2    2/2004
WO   2007089277 A1    8/2007

OTHER PUBLICATIONS

PCT/2006/031177, Dec. 27, 2006, Regents of the Unersity of Minnesota/ ISR.
(Continued)

*Primary Examiner* — Jocelin Tanner
(74) *Attorney, Agent, or Firm* — Emory Patent Group

(57) ABSTRACT

An apparatus includes a component having a shape memory material. The shape memory material has a first shape including a substantially elongate segment. The shape memory material has a second shape including a helix having a first ring and a second ring configured to exert a compressive force on a membrane interleaved between the first ring and the second ring and lying in a plane substan-
(Continued)

tially perpendicular to an axis of the helix, the shape selectable based on an external stimulus.

15 Claims, 8 Drawing Sheets

(58) Field of Classification Search
USPC .............. 606/138, 139, 141, 151–158, 221, 215,606/213, 216, 217; 623/23.72, 23.74–23.76
See application file for complete search history.

(56) References Cited

U.S. PATENT DOCUMENTS

| | | | |
|---|---|---|---|
| 4,224,934 A | | 9/1980 | Scott et al. |
| 5,487,746 A * | | 1/1996 | Yu et al. ................ 606/151 |
| 5,527,356 A | | 6/1996 | Peyman et al. |
| 5,540,701 A * | | 7/1996 | Sharkey et al. ............ 606/153 |
| 5,755,716 A | | 5/1998 | Garito et al. |
| 5,817,075 A | | 10/1998 | Giungo |
| 5,962,027 A | | 10/1999 | Hughes |
| 6,015,417 A * | | 1/2000 | Reynolds, Jr. .............. 606/151 |
| 6,036,678 A | | 3/2000 | Giungo |
| 6,045,791 A | | 4/2000 | Liu |
| 6,156,042 A | | 12/2000 | Aramant |
| 6,165,042 A | | 12/2000 | Chin |
| 6,193,732 B1* | | 2/2001 | Frantzen ............ A61B 17/1227 606/151 |
| 6,402,765 B1* | | 6/2002 | Monassevitch ...... A61B 17/064 606/151 |
| 6,514,238 B1 | | 2/2003 | Hughes |
| 6,896,684 B2* | | 5/2005 | Monassevitch et al. ..... 606/142 |
| 6,955,809 B2 | | 10/2005 | Hughes |
| 2003/0054023 A1 | | 3/2003 | Hughes |
| 2003/0104618 A1 | | 6/2003 | Hughes |
| 2003/0105456 A1 | | 6/2003 | Lin et al. |
| 2004/0039401 A1 | | 2/2004 | Chow et al. |
| 2004/0254567 A1 | | 12/2004 | Holz et al. |
| 2005/0038460 A1* | | 2/2005 | Jayaraman .................. 606/158 |
| 2005/0251154 A1* | | 11/2005 | Chanduszko et al. ........ 606/151 |
| 2005/0267525 A1* | | 12/2005 | Chanduszko ...... A61B 17/0057 606/213 |
| 2006/0002900 A1 | | 1/2006 | Binder et al. |
| 2006/0339993 | | 2/2006 | Hughes |
| 2006/0110428 A1 | | 5/2006 | deJuan et al. |
| 2007/0149989 A1* | | 6/2007 | Santilli .............. A61B 17/1227 606/157 |
| 2007/0179512 A1 | | 8/2007 | Olsen et al. |
| 2009/0118747 A1* | | 5/2009 | Bettuchi et al. .............. 606/151 |
| 2010/0010520 A1* | | 1/2010 | Takahashi et al. ........... 606/157 |

OTHER PUBLICATIONS

PCT/2006/031177, Aug. 5, 2008, Regents of the University of Minnesota/IPRP.
PCT/2006/031177, Jul. 31, 2008, Regents of the University of Minnesota/ Written Op.
2006801125.3, EP, May 5, 2009 Regents of the University of Minnesota/ 94(3) Comm.
2006801125.3, EP, Nov. 2, 2010 Regents of the University of Minnesota/ 94(3) Comm.
2006801125.3, EP, Nov. 3, 2011, Regents of the University of Minnesota/ Response.
2006801125.3, EP, Sep. 10, 2009 Regents of the University of Minnesota/ Response.
Foulds, W.S. "Current and Potential Uses of Partial Choroidectomy," 97th Deutche Opthalmologische Gesellschaft e.V. (DOG) Annual Meeting 1999, [online]. [archived on Apr. 27, 2002]. Retrieved from the Internet: <http://web.archive.org/web/20020427143501/http://www.dog.org/1999/e-abstract99/218.html>.
Joussen, A.M. et al. (Jul. 2006). "Autologous Translocation of the Choroid and Retinal Pigment Epithelium in Age-Related Macular Degeneration," American Journal of Opthalmology, 142(1):17-30.
Stanga, P.E., et al. (2002). "Retinal Pigment Epithelium Translocation After Choroidal Neovascular Membrane Removal in Age-Related Macular Degeneration," Opthalmology, 109(8): 1492-1498.
Van Meurs, J.C. et al. (2003). "Autologous Retinal Pigment Epithelium and Choroid Translocation in Patients with Exudative Age-related Macular Degeneration: Short-term Follow-up." American Journal of Opthalmology. 136(4): 688-695.

* cited by examiner

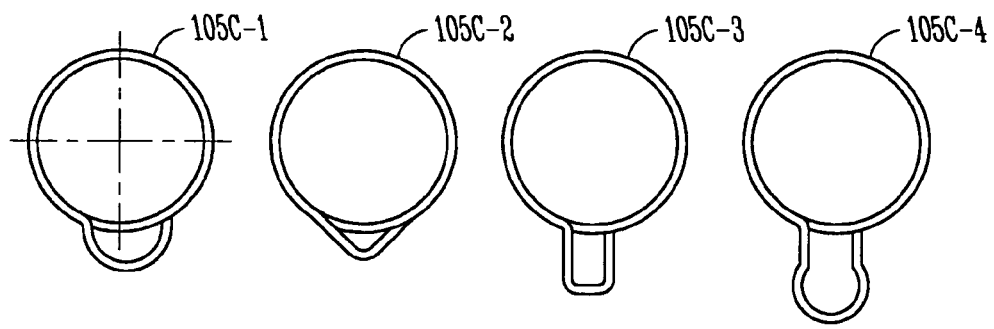
*Fig. 4A*  *Fig. 4B*  *Fig. 4C*  *Fig. 4D*
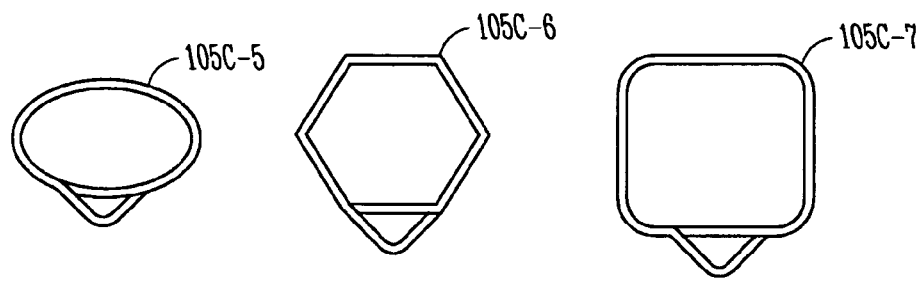
*Fig. 4E*  *Fig. 4F*  *Fig. 4G*
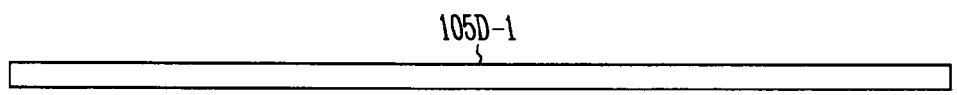
*Fig. 5A*
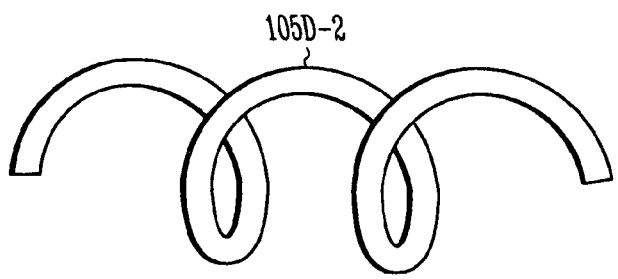
*Fig. 5B*

TISSUE SUPPORT STRUCTURE

CLAIM OF PRIORITY

This patent application claims the benefit of priority, under 35 U.S.C. Section 119(e), to Timothy W. Olsen et al., U.S. Provisional Patent Application Ser. No. 61/264,081, entitled "HELICAL TISSUE SUPPORT STRUCTURE," filed on Nov. 24, 2009, and is incorporated herein by reference.

BACKGROUND

Age-related macular degeneration (AMD) is a disease that causes loss of vision due to deterioration of delicate photo-receptors in a specialized region of the retina known as the macula. The macula is a 1.5 mm region of the retina that has the greatest density of cone photo-receptors in the eye. Surgical correction of AMD involves reconnecting the macula with the healthy choroid by means of a 3-port par plana vitrectomy. The damaged tissue under the macula is replaced with a healthy graft of retinal pigment epithelium (RPE), Bruch's membrane, and partial or full thickness choroid. Unless the graft is supported during cutting and translocation, the tissue can fold on itself and thus damage the delicate cells of the RPE.

Current technology for performing macular translocation is inadequate.

SUMMARY

An example of an apparatus suitable for translocating a tissue graft includes a shape memory material. The shape memory material, such as a metal alloy or a polymer, is configured to transform from a first shape to a second shape upon application of an external stimulus. The first shape can include a substantially elongate segment resembling a section of wire or ribbon. The second shape includes a first structure connected to a second structure in an arrangement that can be described as a helix. The term helix, in general, refers to a continuous series of loops. As described elsewhere in this document, the loops (or structures) of the present subject matter can have various geometric forms or sizes.

The first structure and the second structure (for example, rings) of the second shape are substantially concentric and have a pitch sufficiently small to exert a clamping or compressive force on a membrane disposed between the rings.

A variety of examples are contemplated. In one example, an apparatus has a first shape at the time of insertion in the orifice in the membrane and is configured to transform to a second shape upon activation by an external stimulus. The external stimulus can be provided by RF energy, bipolar electrical energy, or by a laser. The second shape is configured with rings that clamp together on opposing surfaces and retain the membrane (or tissue) in a fixed alignment and orientation.

In various examples, an apparatus is fabricated of material that is responsive to temperature. One example includes a polymer that has a transition temperature equal to approximately that of a human body. In this example, the apparatus is placed in position through the orifice in the membrane while at a different temperature (either above or below body temperature) and the shape transforms to a helical configuration shown in the figures when the temperature of the apparatus reaches approximately body temperature.

While retained by the clamping forces exerted by the rings of the apparatus, a cut can be made in the membrane in the region outside of the rings. The excised membrane can then be manipulated using a forceps or other tool by grasping a feature formed in a portion of the apparatus.

In one example, the separate rings of an apparatus can be connected with a hinge. The hinge, or other type of connection can be activated in a similar manner. Tissue clamping can be facilitated by adherence of the tissue to the rings using thermal energy, by using a clamping mechanical force, or by using some combination of these forces. In addition, the distal end of the rings (opposite the hinge or helical connection) may also be formed in order to mechanically clamp the tissues with a latch mechanism.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 4A, 4B, 4C, 4D, 4E, 4F, and 4G each include a view of an apparatus according to various examples.

FIG. 5A includes a view of an apparatus according to one example.

FIG. 5B includes a view of an apparatus according to one example.

DETAILED DESCRIPTION

Figure 1:
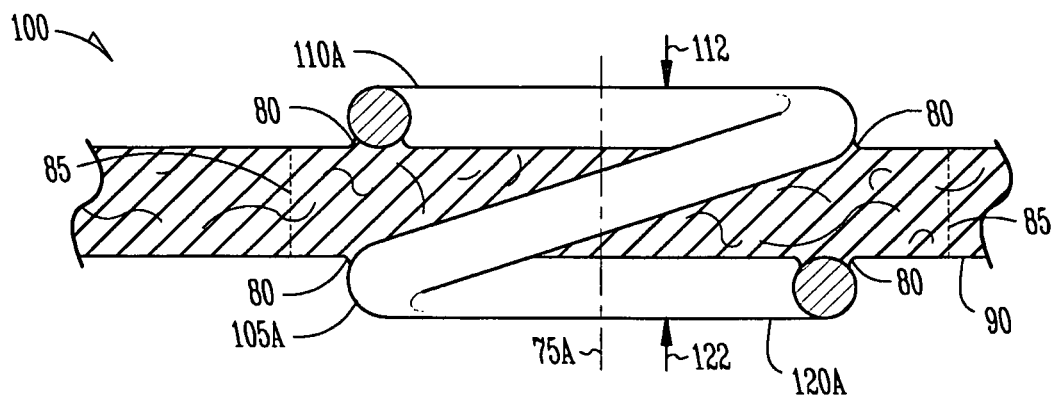
FIG. 1 includes a partial sectional view of a system according to one example.

FIG. 1 includes a view of system 100 according to one example. In the example shown, system 100 includes apparatus 105A. The figure shows an edge view of membrane 90 and a partial section view of apparatus 105A. Apparatus 105A includes first structure 110A continuous with second structure 120A and in the form of a helix. First structure 110A and second structure 120A, in this example, are substantially circular rings concentric with the helix centered on axis 75A and aligned substantially perpendicularly through the plane of the membrane 90 (shown on edge).

Membrane 90 can include tissue (such as live tissue or donor tissue) and in one example, includes a lamination of RPE, Bruch's membrane, and choroid. Membrane 90 can also include artificially engineered tissue or a combination of artificial and natural cellular material, including, for example, stem cells or RPE.

First structure 110A and second structure 120A exert a compressive, or clamping, force on opposing surfaces of membrane 90, as shown by directional arrows 112 and 122, also aligned parallel with axis 75A.

In the figure, apparatus 105A is shown affixed to membrane 90 by bond 80. In one example, bond 80 represents cauterized tissue joining membrane 90 and apparatus 105A. In one example, bond 80 includes a biocompatible adhesive. Other means of bonding apparatus 105A and membrane 90 are also contemplated. For example, radio frequency (RF) energy can be applied to apparatus 105A in order to form a bond with membrane 90. In addition, optical energy provided by a laser or other optical source can be used to form bond 80.

Line 85, through membrane 90, represents a line of separation between the portion of membrane 90 encircled by first structure 110A and second structure 120A and the portion external to first structure 110A and second structure 120A. The interior portion of the membrane can be excised by cutting using, for example, a laser or other surgical tool.

Figure 2:
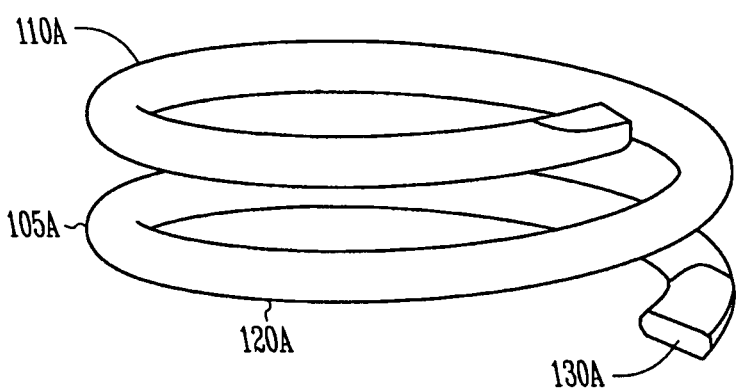
FIG. 2 includes an isometric view of an apparatus according to one example.

In the figure, the rings of first structure 110A and second structure 120A are shown to have substantially the same diameter, however, in one example, the diameters differ. FIG. 2 illustrates a perspective view of apparatus 105A and depicts the generally uniform diameter of first structure 110A and second structure 120A.

Apparatus 105A can have a generally circular cross section that remains uniform throughout the length of the apparatus. The example shown includes a generally round cross section. In one example, the first and second structure are in the form of rings and the rings can be flattened or formed over their circumference or at the ends in a manner to reduce the cross sectional size and reduce bulk. The rounded rectangular cross section can be formed by a die, casting, machining, or by other fabrication technique. Other cross sections are also contemplated. FIG. 2 illustrates end 130A having a flattened cross section.

Figure 3:
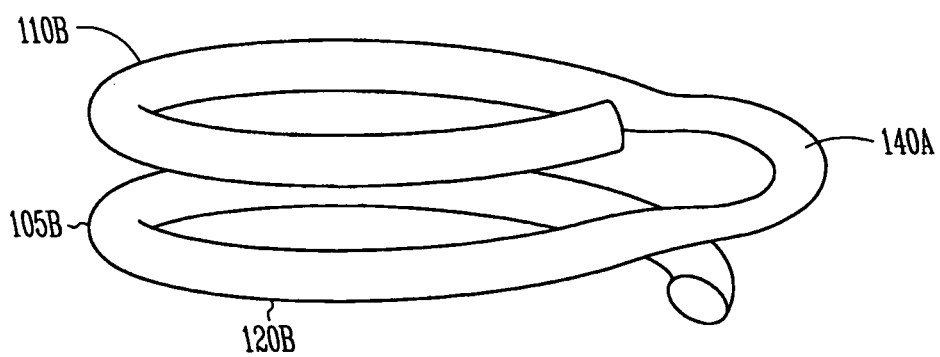
FIG. 3 includes an isometric view of an apparatus according to one example.

FIG. 3 includes an isometric view of apparatus 105B according to one example. In this example, apparatus 105B includes feature 140A. Feature 140A, in the example shown, includes a protuberance that is contiguous with first structure 110B and second structure 120B. Feature 140A can be used to grasp and manipulate apparatus 105B.

FIG. 4A illustrates an example of apparatus 105C-1 having feature 140B. The view illustrated in FIG. 4A depicts the semicircular configuration of feature 140B and the relative diameters corresponding to first structure 110C and feature 140B. FIG. 4A also depicts helix axis 75B as viewed on end, and in this view, the plane of the paper represents the plane of the membrane.

In the examples shown in FIGS. 4A-4G, the feature, in the form of a protuberance, is configured to facilitate manipulation of the apparatus. The protuberance can be tailored to simplify manual tasks such as grasping, moving, and positioning using a forceps or other tool. Examples include a triangle (as shown on apparatus 105C-2 in FIG. 4B), a square (as shown on apparatus 105C-3 in FIG. 4C), a keyhole-shape (as shown on apparatus 105C-4 in FIG. 4D), or other shape.

Protuberance shape complexity can be balanced against considerations of manufacturability. For example, a generally circular protuberance may be easier to manufacture and less convenient to grasp while a large and complex shape may be more difficult to manufacture but may be easier to manipulate. Furthermore, a low profile feature may be easier to manipulate without damaging surrounding tissue.

As noted, FIGS. 4A-4D depict examples in which the clamping force is exerted by a pair of structures that are generally ring-like in configuration. For example, structure 110C (FIG. 4A) includes a nearly complete ring and is continuous with a complementary ring-like structure that is substantially hidden in this view. In addition to a ring, other geometric forms are also possible.

FIGS. 4E-4G illustrate examples of shapes for the structure when viewed on an axis normal to the plane of the membrane. FIG. 4E illustrates an example in which apparatus 105C-5 is substantially oblong or oval in form. FIG. 4F illustrates apparatus 105C-6 having a polygonal form. FIG. 4G illustrates an example of apparatus 105C-7 having a square or, more generally, rectangular, form. Other shapes are also contemplated, including a combination of curved, straight, or oval segments.

A structure can have a form tailored to the shape of the region of the macula. The shape of the structure can be modified to accommodate the pathology. For example, a particular geometric form can be selected to more closely approximate an anatomical pathology. A non-circular shape may reduce challenges associated with tissue clamping. In addition, non-circular shapes may be easier to manufacture as compared with a generally curved shape. The geometric form of the structure may be closed or nearly closed.

In the example shown in FIG. 4G, the corners of the rectangle are rounded and in the example shown in FIG. 4F, the corners of the polygon are sharp. Any corner radius can be used. Sharp corners may cause tissue damage during insertion; however, corners may help increase out-of-plane bending stiffness and thereby minimize deformation during insertion under the tissue. A rounded corner may reduce the incidence of tissue damage.

As noted elsewhere in this document, the apparatus illustrated in each of FIGS. 1, 2, 3, and 4A-4G can include a shape memory material. A shape memory material can include a metal alloy or a polymer that retains a memory of a particular shape. Application of an external stimulus triggers a transformation from a first shape to a second shape. The shape memory material is biocompatible, and in one example, the material is biodegradable.

A variety of shape memory materials are suitable for use in the present subject matter. Examples of shape memory alloys include copper-zinc-aluminum-nickel, copper-aluminum-nickel, and nickel-titanium (NiTi) alloys. In addition to metal alloys, non-metal materials can also be used. For example, a shape memory polymer (including a cross-linked polymer) can be used in the present subject matter.

In addition to the shapes illustrated in each of FIGS. 1, 2, 3, and 4, the present subject matter also includes a mode in which the apparatus shape can be described as substantially elongate. FIG. 5A illustrates a view of an example of apparatus 105D-1 having a substantially elongate segment. In this example, apparatus 105D-1 is generally a straight segment of wire or ribbon. Variations are also contemplated, including an apparatus as illustrated and having an elongate segment that can be gently curved or bent in which a region near an apex is positioned, during a surgical procedure, to align with the membrane. FIG. 5B illustrates an example of apparatus 105D-2 having a ribbon-like cross section and configured in a first shape. In this example, apparatus 105D-2 resembles a stretched segment of a helical spring (such as a SLINKY brand toy) or an orange peeling. In this example, apparatus 105D-2 can transform into a second shape in which the flat sides of the ribbon are stacked in a helical coil with the rings having a radial thickness greater than an axial thickness. Apparatus 105D-2 can be threaded through an aperture in a membrane and upon delivery of an external stimulation, the apparatus transforms to a second shape in which a compressive force is exerted on the membrane.

Figure 6:
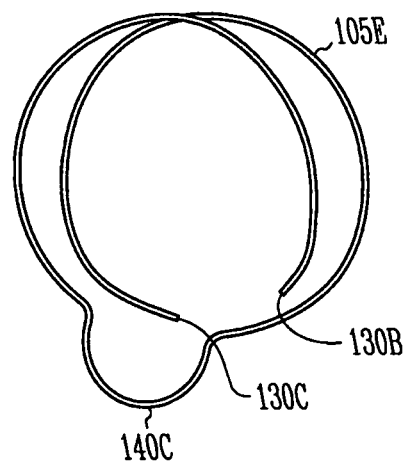
FIG. 6 includes a view of an apparatus according to one example.
Figure 7:
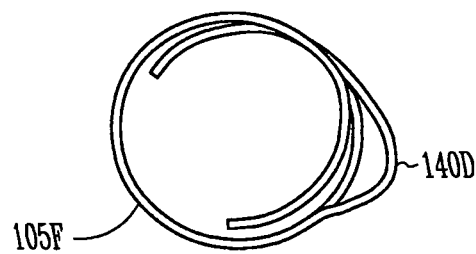
FIG. 7 includes a view of an apparatus according to one example.

FIG. 6 and FIG. 7 depict an apparatus having a shape suitable for exerting a compressive force on a membrane. FIG. 6 includes a view of apparatus 105E according to one example. In this example, apparatus 105E has a substantially helical shape and includes feature 140C. Feature 140C has an effective diameter that is generally smaller than a diameter of the rings of first structure and the second structure.

Relative alignment between end 130B and end 130C is shown in the figure according to one example, however, the position and alignment of end 130B and end 130C can be tailored for a particular application.

FIG. 7 includes a view of apparatus 105F according to one example. The figure illustrates the relative alignment of ends of the rings and illustrates feature 140D. In this example, apparatus 105F is fabricated of shape memory material in the form of a wire.

Apparatus 105F can be fabricated using a coil winder having a diameter tailored to that of the rings of the first structure and the second structure. A shim can be temporarily inserted between fabrication of the first structure and fabrication of the second structure in order to form feature 140D as shown.

When in the second shape, the location of feature 140D is readily apparent. When in the first shape (that is, uncoiled or substantially straight), it may be difficult to identify the location of the unformed feature 140D. In one example, the apparatus can include a mark to help identify the region at which feature 140D will be formed. The marking can include a surface mark, a color difference (a tattoo), a coating, or other element to help distinguish the location of unformed feature 140D. The mark can help a surgeon visually determine the location at which to hold the apparatus during surgery and prior to coiling (following application of external stimulus).

Apparatus 105F, as shown in the figure, has a ring diameter on the order of 3.5 mm to 5 mm, and is fabricated of wire having a diameter of approximately 200 microns, however smaller or larger dimensions are also contemplated. For example, the wire can be formed in a manner similar to a ribbon and have a flat surface of approximately 120 microns. In one example, a cross section of apparatus 105F has rectangular dimensions in the range of 1:3 or 1:4. A wire diameter or ribbon thickness can be selected to be sufficiently thick to exert a meaningful clamping force on the opposing surfaces of the membrane and sufficiently thin to facilitate manipulating without endangering the membrane.

Figure 8:
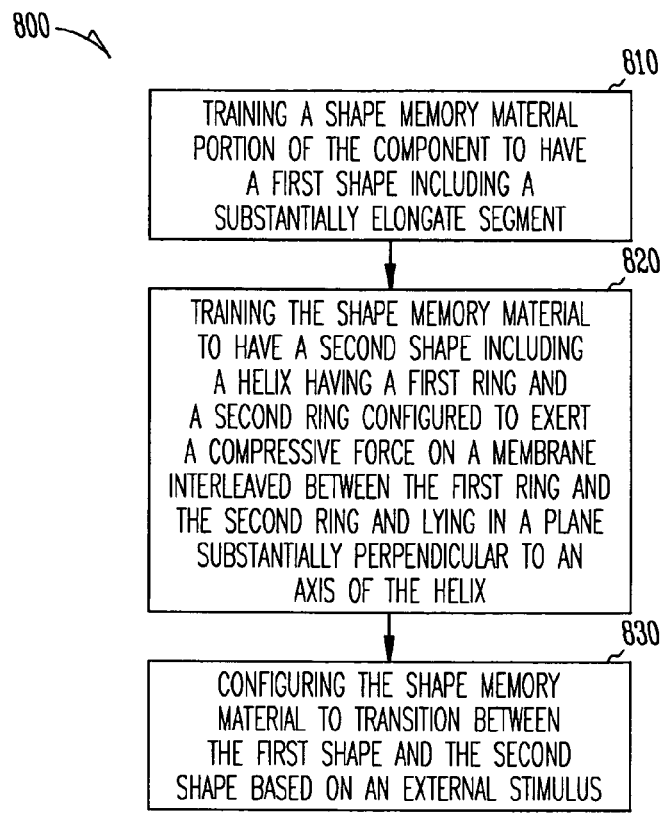
FIGS. 8 and 9 include flow charts for methods according to one example.

In one example, the apparatus has textured surfaces to promote bonding with the membrane. The surface can be textured using a mechanical micromachining (e.g., micro-milled) operation or a die operation. In one example, the texture is produced by forming using a uniaxial compression process to produce a flat surface. FIG. 8 includes flow chart 800 corresponding to a method of forming a component, according to one example. In this example, the component (sometimes referred to herein as an apparatus) is formed of shape memory material configured to transition from a first shape to a second shape in response to application of an external stimulus.

At 810, method 800 includes training a shape memory material portion of the component to have a first shape including a substantially elongate segment.

At 820, method 800 includes training the shape memory material to have a second shape including a helix having a first ring and a second ring configured to exert a compressive force on a membrane interleaved between the first ring and the second ring and lying in a plane substantially perpendicular to an axis of the helix.

At 830, method 800 includes configuring the shape memory material to transition between the first shape and the second shape based on an external stimulus.

Training the shape memory material can include heating or cooling the material to a predetermined temperature while forming the material. The material can include a wire formed of shape memory polymer or a shape memory alloy and training can include forming the wire. The wire can be trained by means of a die, a mold, or other tooling configured to provide a predetermined shape. In this manner, the material is formed with a particular micro structure that is set into memory of the component. An external stimulus can be used to transition between the first shape and the second shape.

In one example, training the shape memory material includes forming a protuberance in the component. The protuberance can be a feature formed in the second shape.

Figure 9:
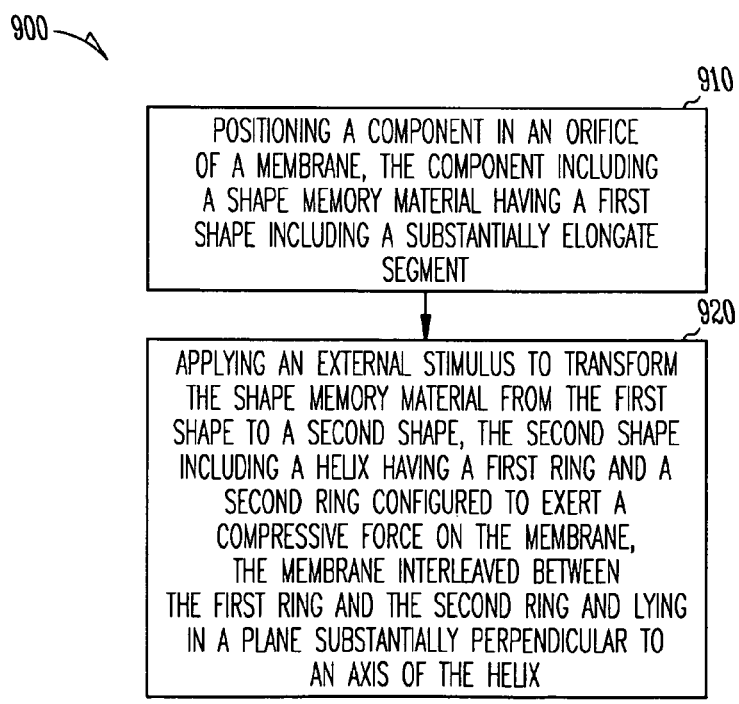

FIG. 9 includes flow chart 900 corresponding to a method of using a component, according to one example. In this example, the component (sometimes referred to herein as an apparatus) is formed of shape memory material configured to transition from a first shape to a second shape in response to application of an external stimulus.

At 910, method 900 includes positioning the component in an orifice of a membrane. The component includes a shape memory material having a first shape that includes a substantially elongate segment and a second shape that includes a helix having a first ring and a second ring and is configured to exert a compressive force on the membrane. The membrane is interleaved between the first ring and the second ring and lies in a plane substantially perpendicular to an axis of the helix.

At 920, method 900 includes applying an external stimulus to transform the shape memory material from the first shape to the second shape. Applying the external stimulus can include applying thermal energy to raise or lower the temperature of the component. In one example, the external stimulus includes an electric field. In addition, the external stimulus can include a magnetic field. Light, such as that provided by a laser or other optical source, can also be used to trigger the transformation. In one example, a predetermined pH level serves as the trigger.

Variations are also contemplated. For example, method 900 can include forming the orifice in the membrane. The orifice can be formed using a laser or a surgical cutting tool. The membrane can include tissue. The tissue can include at least one layer of RPE, Bruch's membrane, or choroid. For example, the tissue can include a layer of RPE and Bruch's membrane.

In one example, a bond is formed between the membrane and the component. The bond can be formed using a laser or formed by application of radio frequency energy using a probe. The probe can be monopolar or bipolar. In one example, bonding includes applying an adhesive at the interface of the component and the membrane.

Following formation of the bond, one example includes excising a portion of the membrane. In FIG. 1, line 85 depicts an example of a cut line. In the figure, cut line 85 is located beyond the periphery of the first structure 110A and the second structure 120A. The cut line encircles at least one of the first structure or the second structure. The separated tissue is held between the first structure 110A and second structure 120A by the compressive forces denoted by arrows 112 and 122.

A tool can be used to grasp the protuberance or other feature. For example, the jaws of a forceps can be used to grasp the feature and thereby manipulate the excised membrane. In addition to a forceps, other hand-operated tools can be used to manipulate the component, and therefore the excised membrane.

Additional Examples

The first structure and the second structure can include rings having a diameter (when viewed in a direction parallel with the axis of the helix) that is substantially matched or have diameters that differ. For example, the RPE is particularly sensitive to damage and thus, a ring disposed on the surface of the RPE can be configured to be larger than a ring on the opposite side of the membrane.

In one example, the first structure and the second structure are coated with a drug or other substance. For example, the structures can be coated with a bonding agent to facilitate affixation of the apparatus on the membrane.

The apparatus can be fabricated using material having a wire-like form. In one example, the material has a uniform cross-section such as a circle, oval, or rectangular shape throughout the length of the material. Other geometric shapes can also be used. In addition, the material can have a flattened surface or faceted surface that facilitates bonding to the membrane.

In addition, the apparatus can have a cross-sectional shape in one portion that differs from a cross-sectional shape of a second portion distributed along the length of the apparatus (in the first shape).

In one example, a physician can form an orifice in the membrane using a cutting tool. The apparatus, while in the first shape, is inserted in the orifice and held in position with an alignment that passes through the membrane. Upon application of an external stimulus (such as thermal energy provided by the body temperature), the apparatus undergoes a transformation from the first shape to a second shape. For example, the first shape can correspond to a straight segment of wire and the second shape can correspond to a helical structure akin to that of a coil spring. In the second shape, adjacent loops of the apparatus are formed on opposing sides of the membrane. The helical-shaped apparatus has a sufficiently small winding pitch to exert a clamping force on the membrane disposed between the adjacent loops. While the membrane is held between the adjacent loops of the helical structure, the physician can make a circular cut about the periphery of the loops and excise the clamped membrane from the surrounding membrane. The clamping force is tailored to retain the excised membrane in fixed alignment and to prevent damage that might be caused by abrasion of a surface of the membrane.

The physician can manipulate the membrane by using a forceps to grasp a feature of the apparatus. The feature can include a protuberance formed in a contiguous segment of the apparatus between the first structure and the second structure.

Figure 10:
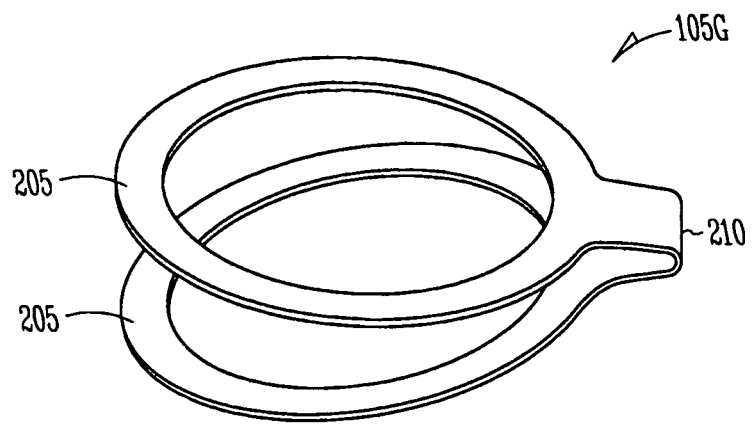
FIGS. 10, 11, and 12 include views of an apparatus according to one example.
Figure 11:
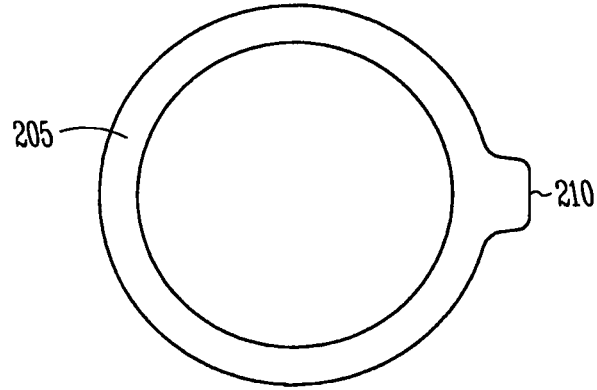
Figure 12:
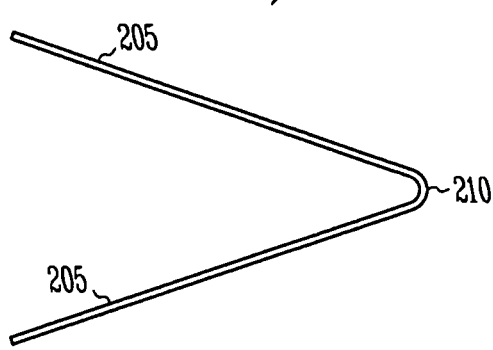
Figure 13:
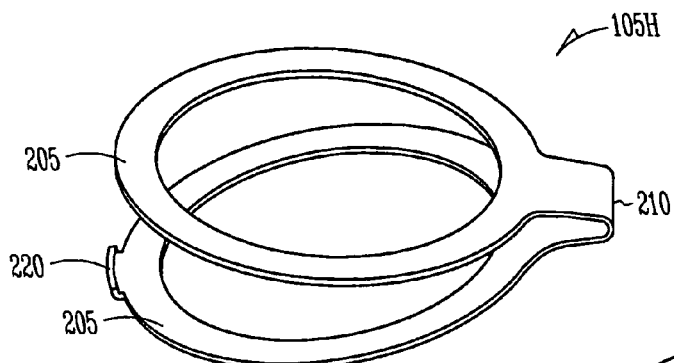
FIGS. 13, 14, 15, and 16 include views of an apparatus according to one example.
Figure 14:
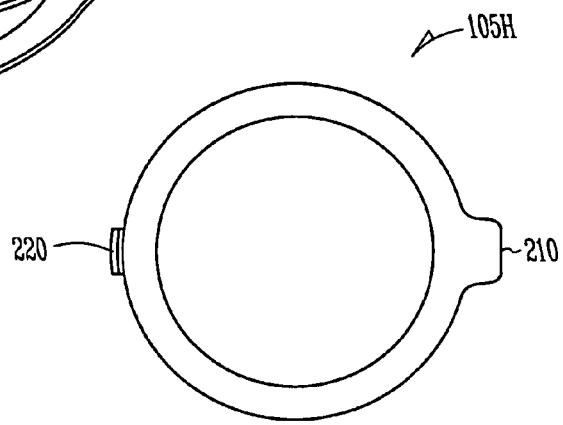

FIGS. 10, 11, and 12 include views of apparatus 105G. Apparatus 105G is fabricated of formed sheet material and thus, has a flattened cross section. For example, apparatus 105G can be fabricated of a foil by laser cutting, etching, stamping, or can be fabricated by a semiconductor fabrication process. A foil provides a good surface area for contacting and bonding with the tissue site. Sharp edges resulting from fabrication can be rounded or radiused to reduce the danger of damaging the tissue.

Apparatus 105G includes rings 205 coupled by link 210. Link 210 can include a hinge or a folded portion of the sheet material or it can be formed of a different material and affixed to rings 205. FIGS. 10, 11, and 12 illustrate a perspective view, a planform view, and an elevation view of apparatus 105G.

In one example, apparatus 105G is fabricated of a shape memory material which can include a shape memory metal (or an alloy of metal, such as nitinol), a polymer, or other material. When activated by an external stimulus, the device can be configured to transform from a first configuration, generally open configuration to a second, generally closed configuration. According to one example, a clamping pressure is exerted on the membrane when apparatus 105G is in the second configuration.

Apparatus 105G can be fabricated of a material having sufficient flexibility and elasticity to allow the material to be rolled into the form of a tube to facilitate insertion in an eye through a small orifice or aperture in the tissue. Following insertion in the eye, the rolled apparatus 105G can be unfurled and thereafter activated to transform into a configuration shown in FIG. 10 or FIG. 12.

FIGS. 13, 14, 15, and 16 illustrate views of apparatus 105H. Apparatus 105H includes rings 205 joined by link 210 as described elsewhere in this document. In addition, apparatus 105H includes latch 220. Latch 220 is formed at a position on ring 205 spaced apart from link 210. Latch 220 can include a feature formed on one ring 205 and configured to engage a second ring 205.

Figure 15:
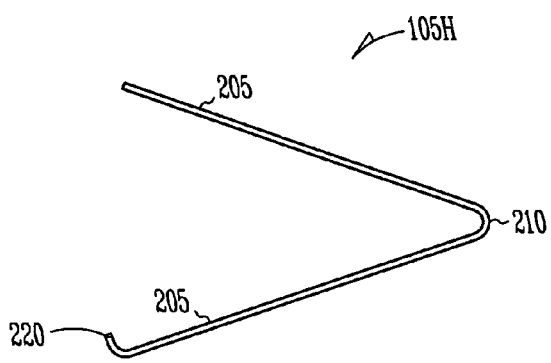
Figure 16:
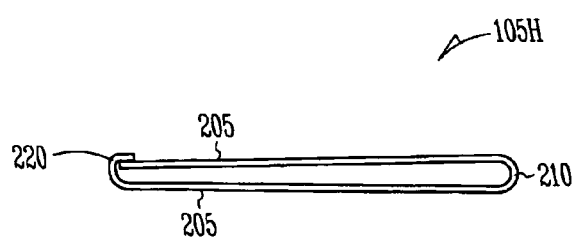

Latch 220, in the example shown, includes a shape memory material and an example of an initial configuration is illustrated in FIG. 15. In the initial configuration, rings 205 can be drawn together to a position that exerts a clamping force on the membrane (not shown). Upon activation by an external stimulus, latch 220 transforms to a second configuration in which rings 205 are retained in a clamped configuration. FIG. 16 illustrates an example in which latch 220 has transformed to a second configuration and rings 205 are retained in a clamped configuration by the combination of link 210 and latch 220.

A variety of materials can be used for fabricating an example of the present subject matter. For example, the material used for fabrication of rings 205, link 210, and latch 220 can be of the same material or of different material. In particular, rings 205, link 210, and latch 220 can all be fabricated of the same material or in another example, link 210 and latch 220 can be fabricated of a shape memory material and rings 205 can be fabricated of a different material.

Figure 17:
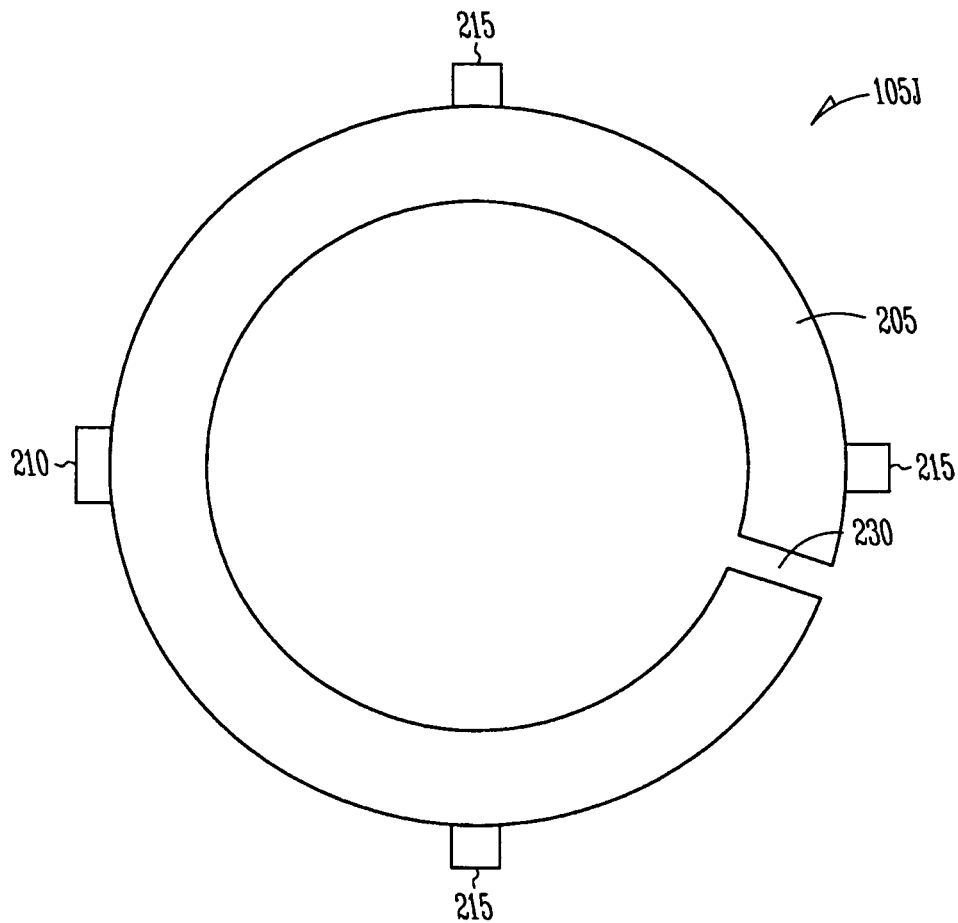
FIGS. 17 and 18 include views of an apparatus according to one example.
Figure 18:
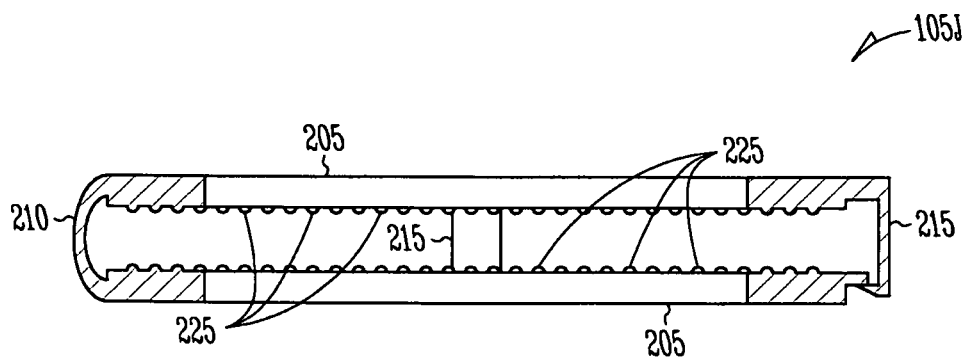

FIG. 17 illustrates a planform view of apparatus 105J and FIG. 18 illustrates an elevation view, according to one example. In the figures, apparatus 105J includes link 210 and three instances of latch 215. Latch 215, in this example, includes a hook feature affixed to a first ring and is configured to engage a corresponding feature of a second ring. In various example, a greater or fewer number of instances of latch 215 are contemplated.

FIG. 17 illustrates gap 230 in a ring of apparatus 105J. Apparatus 105J can be manipulated into an eye by positioning gap 230 in an aperture formed in the eye. Gap 230 represents a discontinuity in ring 205 and allows the adjacent ring ends to be split or separated in a manner to allow apparatus 105J to be threaded through the aperture and into the interior of the eye. Gap 230 is shown as a generally radial void in ring 205, however, other arrangements are also contemplated including a bias cut or angular cut. Gap 230 has sufficiently small circumferential dimensions that it does not impair the bonding of apparatus 105J with the membrane. In the various examples, the ring structure of the apparatus is sufficiently closed such tissue is securely retained and not distorted upon excision.

FIG. 18 illustrates features 225 which represents a texture on the facing surfaces of rings 205. Features 225 can be in the form of individual bumps, ridges, or rings (e.g., concentric rings) that may improve tissue retention and reduce tissue contraction.

Figure 19:
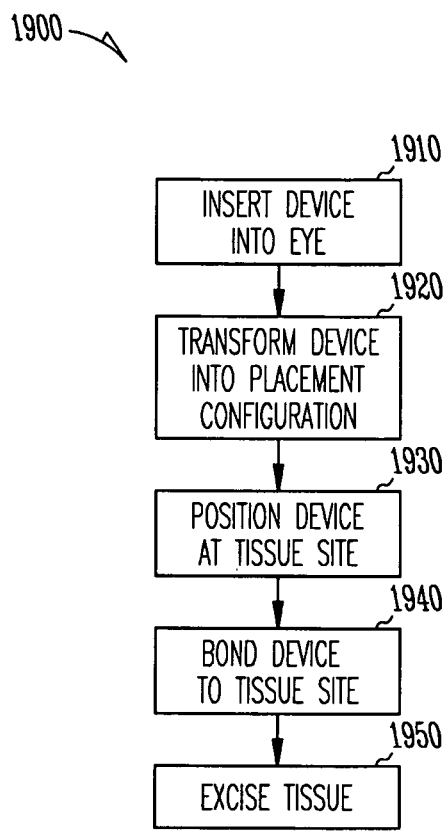
FIG. 19 includes a flow chart for a method according to one example.

The present subject matter can be used for a surgical procedure, an example of which is illustrated in FIG. 19. FIG. 19 depicts method 1900 for using an apparatus, such as apparatus 105J having rings coupled by a link. At 1910, a device (apparatus) is placed into the interior region of an eye. The device can be manipulated into the eye by means of a gap in a ring or by rolling the device into a tubular form and inserting into an aperture of the eye. At 1920, the device is transformed from a first configuration into a second configuration, here referred to as a placement configuration. At the time of insertion, if the device is rolled into a tubular form, then transformation to a placement configuration can include unfurling and folding into a configuration as shown in FIG. 10. In one example, transforming can include activating a shape memory material (such as link 210) using an external stimulus. At 1930, the device is positioned at a tissue site in preparation for excision. This can include manipulating the device through an incision or aperture adjacent a target site in the membrane. In various examples, this can also include aligning the rings of the device with the target and aligning a latch feature with corresponding apertures in the membrane. At 1940, the device is bonded to the tissue site of the membrane. This can include activating a shape memory material in a manner that exerts a physical clamping force on the membrane. In addition, bonding can include cauterizing or otherwise forming a bond (such as with an adhesive) between the device and the membrane. Bonding can also include engaging a textured surface of a device with the membrane. At 1950, the tissue can be excised by laser or surgical methods.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus, comprising:
   a component including:
      a first structure including a distinct geometric shape;
      a second structure including a distinct geometric shape opposing the first structure; and
      a link disposed between the first structure and the second structure, the link being a hinge or folded portion of a material;
   wherein the component is configured to transform between a first configuration and a second configuration;
   wherein the first configuration includes the component being rolled so to have a tube-like shape and the second configuration includes the component being unfurled; and
   wherein in the second configuration, the component is configured to exert a compressive force on a membrane interleaved between the first structure and the second structure.

2. The apparatus of claim 1, wherein:
   each of the first structure and the second structure includes a textured surface configured to bond to the membrane.

3. The apparatus of claim 2, wherein the textured surface includes a plurality of bumps, ridges or rings.

4. The apparatus of claim 1, wherein:
the distinct geometric shape of the first structure and the distinct geometric shape of the second structure are substantially similar.

5. The apparatus of claim 1, wherein the link is configured to cause the component to transform between the first configuration and the second configuration when activated by an external stimulus.

6. The apparatus of claim 5, wherein the external stimulus includes at least one of thermal energy, an electric field, a magnetic field, a light, or a pH level.

7. The apparatus of claim 1, wherein the component includes a latch disposed on the first structure and spaced apart from the link, the latch being configured to engage the second structure.

8. The apparatus of claim 1, wherein:
the first structure and the second structure includes a shape memory material; and
the material of the link is the shape memory material.

9. The apparatus of claim 8, wherein the material includes at least one of a metal alloy or a polymer.

10. The apparatus of claim 1, wherein the geometric shape includes at least one of a circle, a square, a rectangle, an ellipse, an oblong, or a polygon.

11. An apparatus, comprising:
a component including a shape memory material, the component including:
a first structure being a flattened ring;
a second structure being a flattened ring and opposing the first structure;
a link coupled to the first structure and the second structure, the link being a hinge or folded portion of the material; and
a latch disposed on the first structure and spaced apart from the link, the latch being configured to engage the second structure;
wherein:
the first structure and the second structure are configured to be in a clamping configuration;
in the clamping configuration, the first structure and the second structure are configured to exert a compressive force on a membrane interleaved between the first structure and the second structure and lying in a plane substantially parallel to the first structure and second structure; and
the latch is configured to retain the clamping configuration.

12. The apparatus of claim 11, wherein each of the first structure and the second structure includes a textured surface configured to bond to the membrane.

13. The apparatus of claim 12, wherein the textured surface includes a plurality of bumps, ridges or rings.

14. The apparatus of claim 11, wherein:
the component is configured to transform between the clamping configuration and a configuration in which the first structure and the second structure are retained by the latch when activated by an external stimulus, and
the external stimulus includes at least one of thermal energy, an electric field, a magnetic field, a light, or a pH level.

15. The apparatus of claim 11, wherein the shape memory material includes at least one of a metal alloy or a polymer.

* * * * *